United States Patent

Bendler et al.

Patent Number: 5,281,689
Date of Patent: Jan. 25, 1994

[54] POLYCARBONATE FROM BIS[4'-(4-HYDROXYPHENYL)-PHENYL]ALKANES

[75] Inventors: John T. Bendler; John C. Schmidhauser, both of Schenectady; Kathryn L. Longley, Saratoga Springs, all of N.Y.

[73] Assignee: General Electric Company, Schenectady, N.Y.

[21] Appl. No.: 989,310

[22] Filed: Dec. 11, 1992

[51] Int. Cl.$^5$ .............................................. C08G 64/06
[52] U.S. Cl. .................................... 528/196; 528/204; 568/719
[58] Field of Search ................................. 528/196, 204

[56] References Cited

U.S. PATENT DOCUMENTS 3,466,260  9/1969  Bostian et al. ...................... 528/196
5,145,939  9/1992  Nye ..................................... 528/196

Primary Examiner—Harold D. Anderson
Attorney, Agent, or Firm—William H. Pittman

[57] ABSTRACT

Bis[4-(4-hydroxyphenyl)-phenyl]alkanes, as illustrated by 2,2-bis[4-(4-hydroxyphenyl)-phenyl]propane, may be prepared by the reaction of a bisphenol A ester or a similar compound with a p-trialkyltin-substituted anisole, followed by demethylation with a Lewis acid such as boron tribromide. Polycarbonates prepared therefrom are ductile and have high glass transition temperatures.

5 Claims, No Drawings

POLYCARBONATE FROM BIS[4'-(4-HYDROXYPHENYL)-PHENYL]ALKANES

This invention relates to new compositions of matter, and more particularly to new polycarbonates and precursors thereof.

Polycarbonates are a class of high performance engineering resins characterized by optical clarity, high ductility and other advantageous properties. They are frequently employed as lenses and windows by reason of their transparency. Bisphenol A polycarbonate is the principal commercial available resin of this type. It is derived from 2,2-bis(4-hydroxyphenyl) propane, and typically has a glass transition temperature of about 150° C.

It is of increasing interest to prepare polycarbonates which, while retaining the ductility of bisphenol A polycarbonates, have higher glass transition temperatures and are therefore more resistant to softening when heated. Typical areas of application of such polycarbonates are in the preparation of automotive headlamp lenses, which are becoming smaller in size and therefore characterized by closer proximity of the lens to the heat-generating light source, and in windows for aircraft operating at high altitudes, wherein solar heating effects may be pronounced.

The present invention provides a class of ductile polycarbonates having glass transition temperatures typically 30°-40° C. higher than those of bisphenol A polycarbonates. Also provided is a series of bisphenols convertible to said ductile polycarbonates.

In one of its aspects, the invention includes bis[4-(4-hydroxyphenyl)-phenyl]alkanes of the formula

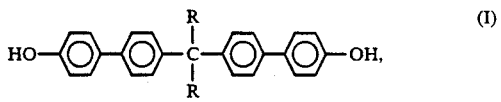

wherein each R is independently a $C_{1-4}$ primary alkyl or $C_{6-10}$ cycloalkyl radical. Thus, the R radicals may each be, for example, methyl, ethyl, propyl, 1-butyl, 2-methylpropyl or cycloheyl. Methyl radicals are preferred.

The bis[4-(4-hydroxyphenyl)-phenyl]alkanes of this invention may be prepared by the conversion of bisphenol A or a homolog thereof to a bis-ester containing readily displaceable groups, such as a bis(trifluoromethanesulfonate), followed by reaction of said bis-ester with a p-trialkyltin-substituted anisole. The latter may be prepared by the reaction of p-bromoanisole with magnesium to form a Grignard reagent, followed by reaction of said Grignard reagent with a trialkyltin halide.

The reaction between the bis-ester and the p-trialkyltin-substituted anisole may be conducted in the presence of a palladium halide-phosphine compound as coupling agent. The product thereof is the bis(methyl ether) of the desired bisphenol, which may be demethylated by reaction with a Lewis acid such as boron tribromide.

The preparation of the bis[4-(4-hydroxyphenyl)-phenyl]alkanes of this invention is illustrated by the following example. Molecular structures were confirmed by spectroscopic methods including infrared, proton and carbon-13 nuclear magnetic resonance spectroscopy and mass spectrometry.

EXAMPLE 1

A solution of 11.4 grams (60 mmol.) of p-bromoanisole in 20 ml. of dry ethyl ether was added dropwise to a stirred mixture of 1.58 grams (66 mmol.) of magnesium turnings in 20 ml. of dry ethyl ether, with the application of mild heat to initiate the Grignard reaction. After 1 hour, the Grignard reagent solution was taken up in a syringe and added slowly to a solution of 21.6 grams (66 mmol.) of tri-n-butyltin chloride in 80 ml. of dry ethyl ether, said solution being maintained at −80° C. by submersion in a solid carbon dioxide-acetone bath. After the addition was complete, the solution was allowed to warm overnight to room temperature and poured into 200 ml. of cold 10% aqueous sulfuric acid solution. The organic layer was separated, washed with water and saturated sodium chloride solution, dried over magnesium sulfate and evaporated to yield the desired p-(tri-n-butyltin)anisole as a dark gold oil. The crude yield was 21.8 grams (92% of theoretical). Upon vacuum distillation, the purified product was obtained as the fraction boiling at 140°-150° C./0.12 torr; the yield thereof was 11.5 grams (48% of theoretical).

A solution of 22.46 grams (79.5 mmol.) of bisphenol A and 75 ml. of pyridine in 200 ml. of methylene chloride was cooled to 0° C., and 50 grams (177 mmol.) of trifluoromethanesulfonic anhydride was added over 40 minutes at a rate to maintain the temperature of the reaction mixture below 10° C. The resulting clear yellow solution was allowed to warm to room temperature, stirred for 14 hours, diluted with methylene chloride and washed twice with 5% aqueous hydrochloric acid solution and three times with water. After drying over magnesium sulfate, the solvent was removed to yield bisphenol A bis(trifluoromethanesulfonate) as a white powder.

A mixture of 10 grams (20.3 mmol.) of the bisphenol A bis(trifluoromethanesulfonate), 5.21 grams (123 mmol.) of lithium chloride, 0.1 gram of butylated hydroxytoluene (as a free radical inhibitor), 700 mg. (1 mmol.) of bis(triphenylphosphine)palladium(II) chloride, 16.30 grams (41 mmol.) of p-(tri-n-butyltin)anisole and 150 ml. of dimethylformamide was stirred at 80° C. under nitrogen for 17 hours, wherein the mixture became tan with suspended gray solids. Upon analysis by high pressure liquid chromatography, complete reaction of the bistrifluoromethanesulfonate was shown to have occurred. The mixture was diluted with ethyl acetate and washed twice with 5% aqueous hydrochloric acid solution, three times with water and once with saturated sodium chloride solution. After drying over magnesium sulfate, the solution was concentrated to give a purple solid which was triturated with hexane to remove tin compounds. The solid residue was purified by flash column chromatography over silica gel, using a mixture of ethyl acetate and hexane, whereupon 2,2-bis[4-(4-methoyphenyl)-phenyl]propane was obtained as a tan solid. The crude yield was 5.21 grams (65% of theoretical). Upon purification by recrystallization from methanol, the product had a melting point of 198°-200° C.

A solution of 5.21 grams (12.8 mmol.) of 2,2-bis(4-methoxybiphenylyl) propane and 6.30 grams (25.5 mmol.) of boron tribromide in 150 ml. of methylene chloride was stirred at room temperature in a nitrogen atmosphere for 18 hours, after which 50 ml. of 10% aqueous sodium hydroxide solution was cautiously added to hydrolyze boron compounds. After ½ hour, the mixture was diluted with an equal volume of ethyl acetate and acidified by the addition of 10% aqueous hydrochloric acid solution. The organic phase was separated, dried over magnesium sulfate and concentrated to give the crude product as yellow flakes. It was eluted through a plug of silica gel and recrystallized from chlorobenzene, to give a crude yield of 2.58 grams (53% of theoretical) of the desired 2,2-bis(4-hydroxybiphenylyl) propane as light tan crystals. Residual color was removed by refluxing for 48 hours in a solution of 2 grams of potassium hydroxide in 30 ml. each of tetrahydrofuran and methanol, followed by flash chromatography over silica gel with a mixture of ethyl acetate and hexane, to give fine white needles with a melting point of 237°–239° C.

The bis[4-(4-hydroxyphenyl)-phenyl]alkanes of this invention may be converted to polycarbonates by reaction with a carbonate source such as phosgene or dimethyl carbonate, using conventional techniques. These include melt polymerization, interfacial polymerization and interfacial conversion to bischloroformate followed by polymerization. Chain termination agents such as phenol may also be employed.

Such polycarbonates are another aspect of the invention; they comprise bis[4-(4-hydroxyphenyl)-phenyl]alkane structural units of the formula

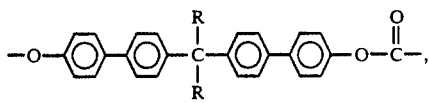

wherein R is as previously defined.

The polycarbonates of this invention include both homopolycarbonates and copolycarbonates. Copolycarbonates typically include, in addition to the aforementioned structural units, units corresponding to the dihydroxy compounds disclosed by name or formula (generic or specific) in U.S. Pat. No. 4,217,438, the disclosure of which is incorporated by reference herein. Such copolycarbonates typically comprise about 25–75% by number of bis[4-(4-hydroxyphenyl)-phenyl]alkane units, with the balance being other units.

Said other units include those having the formula

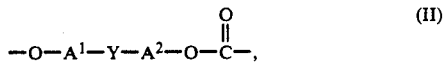

(II)

wherein each of $A^1$ and $A^2$ is a monocyclic divalent aromatic radical and Y is a bridging radical in which one or two atoms separate $A^1$ from $A^2$. The free valence bonds in formula II are usually in the meta or para positions of $A^1$ and $A^2$ in relation to Y.

The $A^1$ and $A^2$ values may be unsubstituted phenylene or substituted derivatives thereof, illustrative substituents (one or more) being alkyl, alkenyl, halo (especially chloro and/or bromo), nitro, alkoxy and the like. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated radical such as methylene, cyclohexylmethylene, 2-[2.2.1]-bicycloheptylmethylene, ethylene, isopropylidene, neopentylidene, cyclohexylidene, cyclopentadecylidene, cyclododecylidene or adamantylidene, especially a gemalkylene (alkylidene) radical. Also included, however, are unsaturated radicals and radicals which contain atoms other than carbon and hydrogen; for example, 2,2-dichloroethylidene, carbonyl, phthalidylidene, oxy, thio, sulfoxy and sulfone. For reasons of availability and particular suitability for the purposes of this invention, the preferred units of formula II are 2,2-bis(4-phenylene)propane carbonate units, which are derived from bisphenol A and in which Y is isopropylidene and $A^1$ and $A^2$ are each p-phenylene.

The preparation of the polycarbonates of this invention is illustrated by the following examples. Molecular weights were determined by gel permeation chromatography relative to polystyrene.

EXAMPLE 2

Phosgene was passed for 4 minutes at 300 mg. per minute through a solution of 500 mg. (1.3 mmol.) of 2,2-bis[4-(4-hydroxyphenyl)-phenyl]propane, 300 mg. (1.3 mmol.) of bisphenol A and 15 ml. of pyridine in 60 ml. of methylene chloride. The yellow solution was then purged with nitrogen for 45 minutes, washed twice with 5% aqueous hydrochloric acid solution and three times with water, and dried over magnesium sulfate. It was finally filtered and poured into methanol. Upon filtration and drying under vacuum, there was obtained 500 mg. of copolycarbonate as a pink powder having a weight average molecular weight of 18,100 and a dispersivity of 2.70. Differential scanning calorimetry showed a glass transition temperature of 178° C.

EXAMPLE 3

A mixture of 500 mg. (1.3 mmol.) of 2,2-bis(4-hydroxybiphenylyl)propane, 300 mg. (1.3 mmol.) of bisphenol A, 50 ml. of methylene chloride, 40 ml. of water, 0.6 ml. of a 5% w/v triethylamine solution in methylene chloride and 0.075 ml. of a 5% w/v solution of phenol in methylene chloride was prepared and its pH was adjusted to 12.8 by the addition of 10% aqueous sodium hydroxide solution. The mixture was stirred for 5 minutes, after which phosgene was added over 10 minutes at a flow rate of 300 mg. per minute, while the pH was maintained between 10 and 12 by the addition of further sodium hydroxide solution. After purging with nitrogen for 20 minutes, the mixture was diluted with methylene chloride and washed with 5% aqueous hydrochloric acid solution and three times with water. It was dried over magnesium sulfate, filtered and poured into methanol, and the solid which separated was swelled with methylene chloride and reprecipitated by the addition of acetonitrile. Upon drying in vacuum, there was obtained 650 mg. of the desired copolycarbonate; it had a weight average molecular weight of 203,000, a dispersivity of 1.5 and a glass transition temperature of 190° C.

What is claimed is:

1. A polycarbonate comprising structural units of the formula

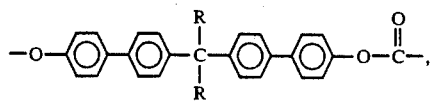

wherein each R is independently a $C_{1-4}$ primary alkyl radical.

2. A polycarbonate according to claim 1 which is a copolycarbonate also containing structural units of the formula

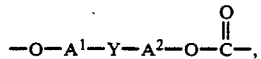

wherein each $A^1$ and $A^2$ is a monocyclic divalent aromatic radical and Y is a bridging radical in which 1 or 2 atoms separate $A^1$ from $A^2$.

3. A copolycarbonate according to claim 2 wherein comprises about 25-75% by number of said units of the formula

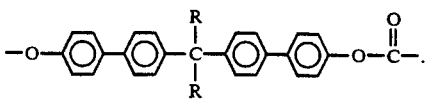

4. A copolycarbonate according to claim 3 wherein each R is methyl.

5. A copolycarbonate according to claim 3 wherein each of $A^1$ and $A^2$ is p-phenylene and Y is isopropylidene.

* * * * *